(12) United States Patent
Ikeda (10) Patent No.: US 8,076,161 B2
(45) Date of Patent: Dec. 13, 2011

(54) TARGET SUBSTANCE DETECTION KIT AND TARGET SUBSTANCE DETECTION METHOD

(75) Inventor: Takashi Ikeda, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 657 days.

(21) Appl. No.: 12/120,514

(22) Filed: May 14, 2008

(65) Prior Publication Data

US 2009/0021250 A1    Jan. 22, 2009

(30) Foreign Application Priority Data

May 31, 2007    (JP) .................................. 2007-145288

(51) Int. Cl.
*G01N 33/553* (2006.01)
(52) U.S. Cl. ...................................................... 436/526
(58) Field of Classification Search .................. 436/526
See application file for complete search history.

(56) References Cited

U.S. PATENT DOCUMENTS

| | | | | |
|---|---|---|---|---|
| 4,725,140 | A * | 2/1988 | Musha | 356/336 |
| 6,979,574 | B1 * | 12/2005 | Kotitz et al. | 436/526 |
| 7,387,901 | B2 | 6/2008 | Nishiuma et al. | |
| 7,639,359 | B2 * | 12/2009 | Chung et al. | 356/338 |
| 2007/0231926 | A1 | 10/2007 | Ikeda | |
| 2007/0237673 | A1 | 10/2007 | Ikeda et al. | |
| 2007/0298510 | A1 | 12/2007 | Imamura et al. | |
| 2008/0225292 | A1 | 9/2008 | Nishiuma et al. | |

OTHER PUBLICATIONS

U.S. Appl. No. 12/135,982, filed Jun. 9, 2008, Kazuhisa Okano, et al.
U.S. Appl. No. 12/054,231, filed Mar. 24, 2008, Masaru Kaieda, et al.
David R. Baselt, et al., "A biosensor based on magnetoresistance technology", Biosensors & Bioelectronics, vol. 13 (1998), pp. 731-739.
D. L. Graham, et al., "High sensitivity detection of molecular recognition using magnetically labelled biomolecules and magnetoresistive sensors", Biosensors & Bioelectronics, vol. 18 (2003), pp. 483-488.
Pierre-A. Besse, et al., "Detection of a single magnetic microbead using a miniaturized silicon Hall sensor" Applied Physics Letters, vol. 80, No. 22 (2002) pp. 4199-4201.
Oyo Buturi, Biological immunoassay with magnetic marker and squid magnetometer, The Japanese Society of Applied Physics, vol. 73, No. 1 (2004), Abstract.
K. Enpuku, et al., "High-Tc SQUID system for biological immunoassays", Physica C, 357-360, 2001, pp. 1462-1465.

* cited by examiner

*Primary Examiner* — Mark Shibuya
*Assistant Examiner* — Pensee Do
(74) *Attorney, Agent, or Firm* — Fitzpatrick, Cella, Harper & Scinto (57) ABSTRACT

The present invention allows a target substance to be detected easily without applying an external magnetic field to a magnetic marker. The present invention provides a target substance detection kit including: a target substance detection board which contains a magnetic sensor and a first target substance capture molecule; and a magnetic marker which contains a magnetic structure and a second target substance capture molecule, wherein the first target substance capture molecule exists on a surface of the target substance detection board, and the magnetic structure generates a magnetic stray field under polarized light.

4 Claims, 7 Drawing Sheets

TARGET SUBSTANCE DETECTION KIT AND TARGET SUBSTANCE DETECTION METHOD

BACKGROUND OF THE INVENTION

1. Field of the Invention

The present invention relates to a target substance detection kit and target substance detection method.

2. Description of the Related Art

Recently, methods for easily detecting a trace quantity of magnetic particles using a magnetoresistive device have been proposed, the magnetic particles being used as marker objects (see, for example, David R. Baselt, et al., Biosensors & Bioelectronics 13, 731, 1998; D. L. Graham, et. al., Biosensors & Bioelectronics 18, 483, 2003).

David R. Baselt, et al. (1998) used giant magnetoresistive (GMR) devices measuring 80 µm×5 µm and 20 µm×5 µm as a magnetic sensor to detect multiple magnetic particles 2.8 µm in diameter. Magnetic films used for GMR devices are in-plane magnetization films and a magnetic field applied to the magnetic particles is applied to the magnetic films in a direction perpendicular to film surfaces. Consequently, magnetic stray fields emitted by the magnetic particles magnetized by the application of the magnetic field are applied to the magnetic films of the GMR devices approximately along a film plane and magnetization of the magnetic films is aligned with a direction of the magnetic field. The magnetic field used to magnetize magnetic particles in the manner described above is generally known as a biasing magnetic field.

Magnitude of electrical resistance of a magnetoresistive device depends on relative magnetization directions of two magnetic films. Specifically, the electrical resistance is relatively small when the magnetization directions are parallel and is relatively large when the magnetization directions are antiparallel. To bring about parallel and antiparallel magnetization states, one of the two magnetic films of the magnetoresistive device has its magnetization direction fixed and the other magnetic film is made of a magnetic material which has such a coercive force that the magnetic field of the magnetic material can be reversed by the magnetic stray fields of the magnetic particles. If no magnetic particle exists on the magnetoresistive device configured in this way, no magnetic reversal occurs because application of a biasing magnetic field will not cause a magnetic field to be applied along the film plane.

Also, a detection circuit proposed by David R. Baselt, et al. (1998) includes a bridge circuit made up of two fixed resistors, a GMR device on which magnetic particles are not fixed, and a GMR device on which magnetic particles can be fixed. The detection circuit detects a potential induced in the bridge circuit, using a lock-in amplifier.

D. L. Graham, et. al. (2003) used GMR devices measuring 2 µm×6 µm with in-plane magnetization films to detect a magnetic particle 2 µm in diameter. As is the case with David R. Baselt, et al. (1998), D. L. Graham, et. al. (2003) detected a magnetic particle by comparing output signals of two GMR devices placed side by side: a GMR device on which a magnetic particle can be fixed and a GMR device on which a magnetic particle is not fixed. However, a magnetic field was applied to the magnetic particle in a longitudinal in-plane direction of the magnetic films.

As described above, methods for detecting magnetic particles using magnetoresistive devices detect the magnetic particles by magnetizing the magnetic particles in a desired direction and varying the magnetization direction of the magnetoresistive device using magnetic stray fields emitted by the magnetic particles. These methods are easy to handle and enable detection in a relatively short time.

The magnetic particle is fixed to a sensor, for example, using an antigen-antibody reaction if a target substance to be detected is an antigen. Specifically, a primary antibody formed on the sensor is allowed to react with a specimen such as blood which may contain an antigen. Then the magnetic particle modified by a secondary antibody is allowed to react with the specimen. If there is an antigen in the specimen which is obtained by the series of operations, there will be binding among the primary antibody, antigen, secondary antibody, and magnetic particle. If there is no antigen, no such binding will occur, and consequently, the magnetic particle will not be fixed to the sensor.

With this fixing method, one magnetic particle per target substance is fixed to the sensor, and thus a single target substance can be detected by means of a highly sensitive magnetic sensor.

Being similar to the sensing method using a magnetoresistive device, a method for detecting magnetic particles using a Hall device as a magnetic sensor has been proposed (see, for example, Pierre-A. Besse, et al., Appl. Phys. Let. 22, 4199, 2002).

Pierre-A. Besse, et al. (2002) magnetized a 2.8-µm-diameter magnetic bead placed just above a Hall device by the application of a DC magnetic field, changed the magnetization direction of the magnetic bead by the application of an AC magnetic field, and thereby detected the magnetic bead. When a magnetic field is applied in a z-axis direction with an electric current being passed along the film plane direction of the Hall device, electrons are subjected to a Lorentz force, causing a potential to be produced in a direction orthogonal to the electric current in the film plane.

The potential is proportional to magnetic field strength, and thus the potential due to Hall effect changes with changes in the magnetization direction of the magnetic bead. Since no magnetic stray field is produced without a magnetic bead, the magnitude of the magnetic field applied to the Hall device varies with the presence or absence of a magnetic bead, and so does the magnitude of the potential. This means that the presence or absence of a magnetic bead can be detected by a Hall device.

Also, a method which detects magnetic particles using a superconducting quantum interference device has been proposed (see, for example, K. Enpuku, "Biological immunoassay with magnetic marker and SQUID magnetometer," OYO BUTURI Vol. 73, No. 1 (2004), p. 28 (the Japan Society of Applied Physics)). According to this method, the magnetic particles are fastened to a detection area and aligned in terms of their magnetization direction by the application of a magnetic field. The magnetic stray fields emitted by the magnetic particles are detected by a Josephson device to determine quantity of the magnetic particles. However, to eliminate impacts of the applied magnetic field, the superconducting quantum interference device has to be placed parallel to the applied magnetic field so as not to cross the applied magnetic field.

To detect magnetic particles, it is desirable that the magnetic stray fields emitted by the magnetic particles are large, but small magnetic particles, whose magnetization is not saturated in zero magnetic field, produce small magnetic stray fields. Also, in the medical field, when desired biomolecules are extracted from a specimen solution such as blood or when magnetic particles are used for a biosensor currently under study, desirably the magnetic particles are dispersed when dropped in the specimen solution. For that, it is desirable that the magnetization is very weak. In zero magnetic field, some magnetic particles are superparamagnetic without magnetization. To detect such weakly magnetized magnetic particles, it is necessary to align the magnetization of the magnetic particles in one direction by the application of an external magnetic field as described above.

However, it is not desirable to detect minute magnetic stray fields emitted by magnetic particles by applying a large magnetic field to the magnetic sensor. To detect particularly small magnetic stray fields, it is necessary to devise measures such as preparing two magnetic sensors, fixing magnetic particles to only one of the magnetic sensors with the other magnetic sensor used as a reference, and detecting a difference in signals of the two sensors by means of a sense amplifier. Furthermore, when using magnetic sensors which give a small detection signal, it may also be necessary to incorporate the magnetic sensors into a Wheatstone bridge circuit. When using a magnetoresistive device or Hall device as a magnetic sensor, it is necessary to strictly control the direction of a biasing magnetic field to reduce variation in the detection signal. This is true especially when using a superconducting quantum interference device which has very high magnetic field sensitivity.

SUMMARY OF THE INVENTION

The present invention provides a sensor which can easily detect a target substance without applying an external magnetic field to a magnetic marker.

The present invention provides a target substance detection kit comprising: a target substance detection board which contains a magnetic sensor and a first target substance capturing body; and a magnetic marker which contains a magnetic structure and a second target substance capturing body, wherein the first target substance capturing body exists on a surface of the target substance detection board, and the magnetic structure generates a magnetic stray field under polarized light.

Desirably, the magnetic sensor is of a type whose electrical characteristics are changed by the magnetic stray field generated by the magnetic structure.

Desirably, the magnetic sensor is one of a magnetoresistive device, a Hall device, and a superconducting quantum interference device.

Also, the present invention provides a target substance detection method for detecting the presence or absence of a target substance or an amount of the target substance in a specimen, comprising: (i) putting a magnetic marker and the specimen in contact with a target substance detection board which contains a magnetic sensor and a first target substance capturing body and thereby forming a compound which includes the first target substance capturing body, the target substance, and the magnetic marker, the magnetic marker containing a magnetic structure and a second target substance capturing body; (ii) illuminating the compound with polarized light; and (iii) detecting a magnetic stray field generated by the magnetic structure under the polarized light.

Desirably, the detecting a magnetic stray field generated by the magnetic structure under the polarized light detects changes in electrical characteristics of the magnetic sensor, the changes being caused by the magnetic stray field generated by the magnetic structure under the polarized light.

Desirably, the polarized light is a circular polarized light.

Desirably, the magnetic sensor is one of a magnetoresistive device, a Hall device, and a superconducting quantum interference device.

Also, the present invention provides a sensor which detects a to-be-detected object whose magnetization changes under illumination with polarized light, comprising: a light source which illuminates the to-be-detected object with polarized light; and a magnetic sensor which detects a magnetic stray field generated by the change in the magnetization of the to-be-detected object illuminated with the polarized light from the light source.

Desirably, the sensor further comprises a detection circuit which detects changes in characteristics of the magnetic sensor, wherein electrical characteristics of the magnetic sensor change according to the magnetic stray field generated by the to-be-detected object.

Desirably, the to-be-detected object is fixed in a sensing area of the magnetic sensor via a medium and detected by the magnetic sensor, allowing quantity of the medium to be detected indirectly.

Desirably, the light source varies the polarized light which illuminates the to-be-detected object; and the characteristics of the magnetic sensor change according to the magnetic stray field which changes with changes in the polarized light from the light source.

Desirably, the magnetic sensor is a device which exhibits magnetoresistance.

Desirably, the magnetic sensor is a device which exhibits Hall effect.

Desirably, the magnetic sensor is a Josephson device.

Desirably, the medium is biomolecules.

Desirably, the to-be-detected object is a magnetic body.

Desirably, the polarized light which illuminates the to-be-detected object from the light source is circular polarized light.

Further features of the present invention will become apparent from the following description of exemplary embodiments with reference to the attached drawings.

DESCRIPTION OF THE EMBODIMENTS

Embodiments of the present invention will be described in detail below with reference to the drawings.

A first aspect of the present invention is a target substance detection kit comprising: a target substance detection board which contains a magnetic sensor and a first target substance capturing body; and a magnetic marker which contains a magnetic structure and a second target substance capturing body, wherein the first target substance capturing body exists on a surface of the target substance detection board, and the magnetic structure generates a magnetic stray field under polarized light.

Detailed description will be given below with reference to drawings.

Figure 1:
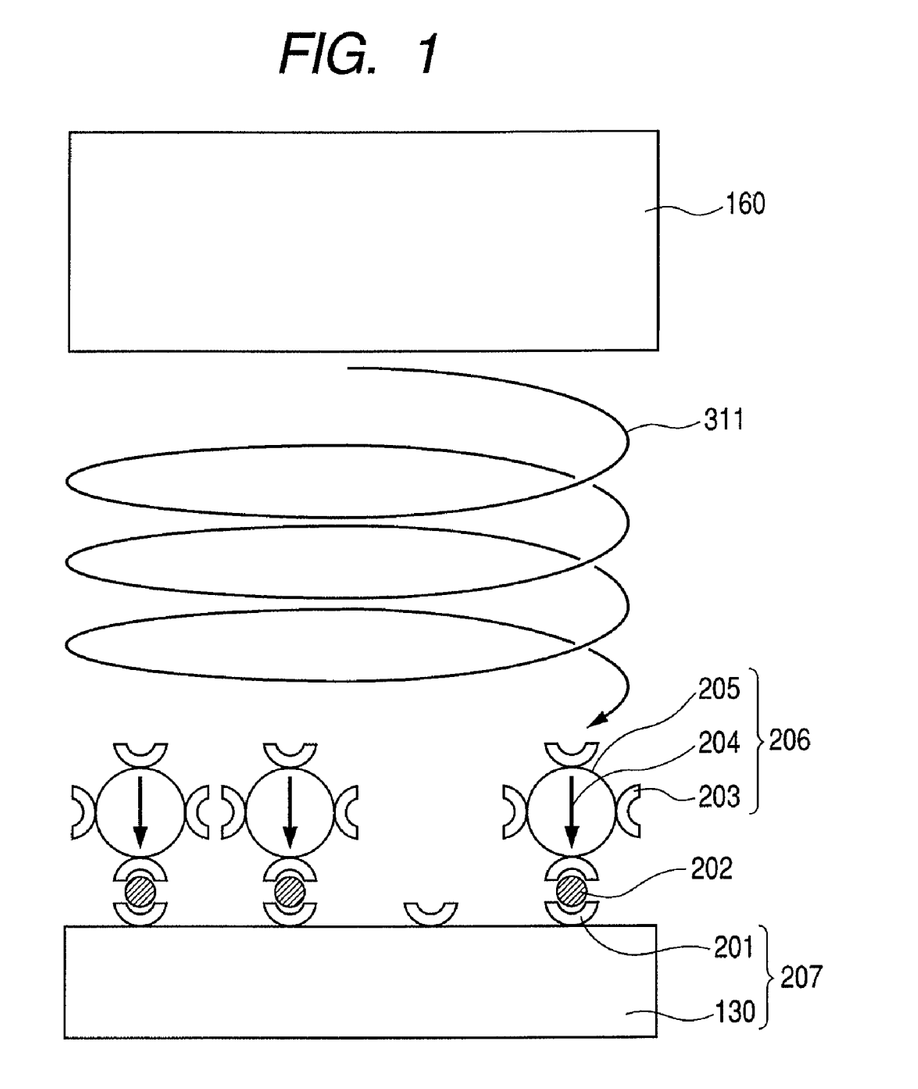
FIG. 1 is a conceptual diagram illustrating a target substance detection kit and target substance detection method according to the present invention.

FIG. 1 shows a light source 160, a magnetic sensor 130, a first target substance capturing body 201, a target substance 202, a target substance detection board 207, a polarized light 311, and magnetic markers 206 each of which includes a magnetic structure 205 and a second target substance capturing body 203.

The first target substance capture molecule 201 of the target substance detection board 207 traps the magnetic markers 206—which include the magnetic structure 205, target substance 202, and second target substance capturing body 203—using interaction between the first target substance capturing body 201 and target substance 202. Then, when the magnetic markers 206 are illuminated with the polarized light 311 generated by the light source 160, a magnetic vector 204 is produced in the magnetic structure 205 of each magnetic marker 206, generating a magnetic stray field. The target substance can be detected when the magnetic stray field is detected using the magnetic sensor 130 of the target substance detection board 207.

Various components of a target substance detection kit will be described.

<Target Substance Detection Board>

The target substance detection board 207 includes the magnetic sensor 130 and the first target substance capturing body 201 which traps the target substance 202 fixed to a surface of the magnetic sensor 130.

Physical quantities of the magnetic sensor 130 such as electrical resistance, potential, and electromotive force are changed by the magnetic stray field generated by the magnetic structures 205 illuminated with the polarized light 311. The devices whose physical quantities are changed by a magnetic field include magnetoresistive devices such as GMR devices and TMR (tunnel magnetic resistance) devices, Hall devices, and superconducting quantum interference devices.

Figure 2:
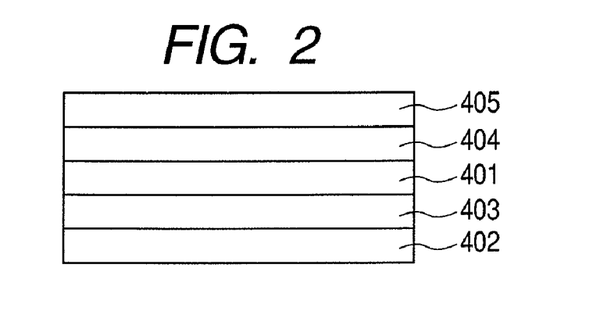
FIG. 2 is a conceptual diagram for describing a film configuration of a magnetoresistive device.
Figure 3:
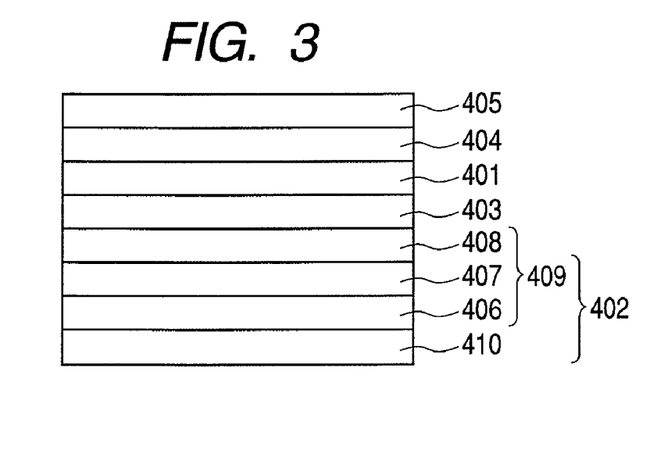
FIG. 3 is a conceptual diagram illustrating a magnetoresistive device which has an artificial antiferromagnetic film structure.

As illustrated in FIG. 2, the magnetoresistive device has a structure in which an intermediate layer 403 of nonmagnetic film is sandwiched between a magnetic film known as a free layer 401 and a magnetic film known as a pinned layer 402. The two magnetic layers have different magnetic properties. The pinned layer 402 has its magnetization direction fixed in a desired direction while the free layer 401 allows its magnetization direction to be changed easily by the application of a magnetic field. The intermediate layer 403 may be a conductive film of Cu or other metal, or a dielectric film of MgO, $Al_2O_3$, or the like. However, when a dielectric film is used as the intermediate layer 403, the film has to be a tunnel barrier film which allows electrons to tunnel through in a film thickness direction. When a metal film is used as the intermediate layer 403, the magnetoresistive device is referred to as a GMR device. On the other hand, when a tunnel barrier film is used as the intermediate layer 403, the magnetoresistive device is referred to as a TMR device. It is desirable to use MgO of a single-crystal structure as the tunnel barrier film because of great changes produced in the electrical resistance of the magnetoresistive device. The pinned layer 402 often has a structure in which an antiferromagnetic film is exchange-coupled to a ferromagnetic film formed in contact with an undersurface of the tunnel barrier film. Also, MgO film of a single-crystal structure for use as the tunnel barrier film can be prepared easily using an amorphous structure for the ferromagnetic film formed in contact with the undersurface of the MgO film. Furthermore, as shown in FIG. 3, the ferromagnetic film of the pinned layer 402 may be formed by exchange-coupling an artificial antiferromagnetic film 409 and antiferromagnetic film 410 to each other, where the artificial antiferromagnetic film 409 is formed by stacking a ferromagnetic film 406, metal film 407, and ferromagnetic film 408 in sequence. This reduces magnetostatic coupling between the free layer 401 and pinned layer 402 at film edges caused by free magnetization. When using ferromagnetic film of the pinned layer 402 as the antiferromagnetic layer, it is desirable to use Ru for the metal film 407 formed between the ferromagnetic films 406 and 408. Any material may be used for the antiferromagnetic film 410 as long as the magnetization direction of the ferromagnetic film exchange-coupled to the antiferromagnetic film 410 can be fixed within an operating temperature range. If operating temperature is around room temperature, for example, MnPt, MnIr, or NiO can be used for the antiferromagnetic film 410. On the other hand, transition metal such as Fe, Co, or Ni or an alloy thereof can be used for the ferromagnetic films 406 and 408 of the pinned layer 402. Incidentally, Cr or B may be added to the transition metal or alloy of transition metals to obtain the ferromagnetic film 408 of amorphous structure. Desirably, a magnetic film having a low coercive force is used as the free layer 401. For example, NiFe (Permalloy) or CoFeB can be used for such a magnetic film.

Generally, magnetic layers are often made of easily oxidizable material, and thus it is desirable that surfaces of magnetic films are covered with a protective film. Therefore, desirably a protective layer 404 is formed on a surface of the magnetoresistive device so that the free layer 401 will not be exposed to the atmosphere or a test solution. Any material may be used as constituent material of the protective layer 404 as long as the material is impermeable to oxygen and other substances which can oxidize the magnetic film. However, noble metal is desirable because the noble metal can stably protect the magnetic film against many substances. Also, a fixing layer 405 capable of fixing target substance capturing bodies is formed on a surface of the protective layer 404 to fix the target substance capturing bodies on the surface of the magnetoresistive device. The fixing layer 405 is selected as required depending on the target substance capturing bodies. If there are thiol groups at ends of the capturing bodies, the fixing layer 405 may be made of Au or the like.

Figure 4:
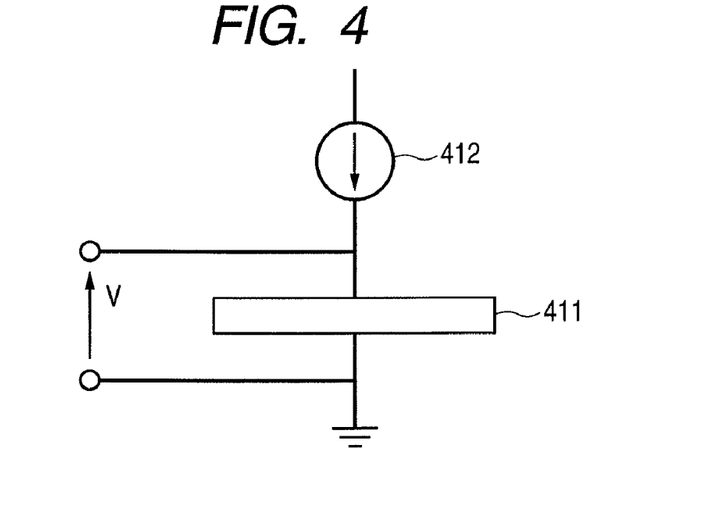
FIG. 4 is a conceptual diagram illustrating a connection example of a detection circuit when a magnetoresistive device is used as a magnetic sensor.

Magnetoresistive devices sense magnetic fields by passing an electric current. Among magnetoresistive devices, TMR devices need to pass an electric current in the film thickness direction of the devices by being wired in such a way that a voltage will be applied in the film thickness direction of a tunnel barrier film in order to allow electrons to pass through the tunnel barrier film. On the other hand, in the case of GMR devices, an electric current may be passed in any direction, but the largest resistance change is obtained when the electric current is passed in the film thickness direction of the devices. Thus, when a magnetoresistive device 411 is used as a magnetic sensor device, a constant current source 412 is connected to detect a voltage across the magnetoresistive device 411, for example, as shown in FIG. 4.

Figure 5:
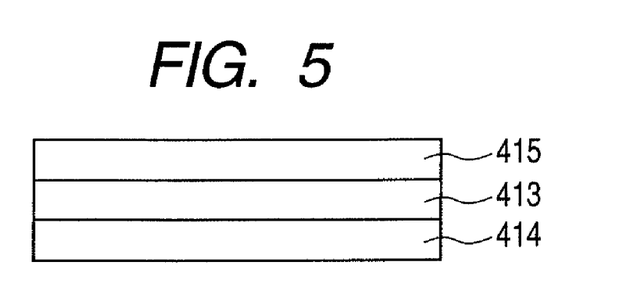
FIG. 5 is a conceptual diagram for describing a film configuration of a Josephson device.
Figure 6:
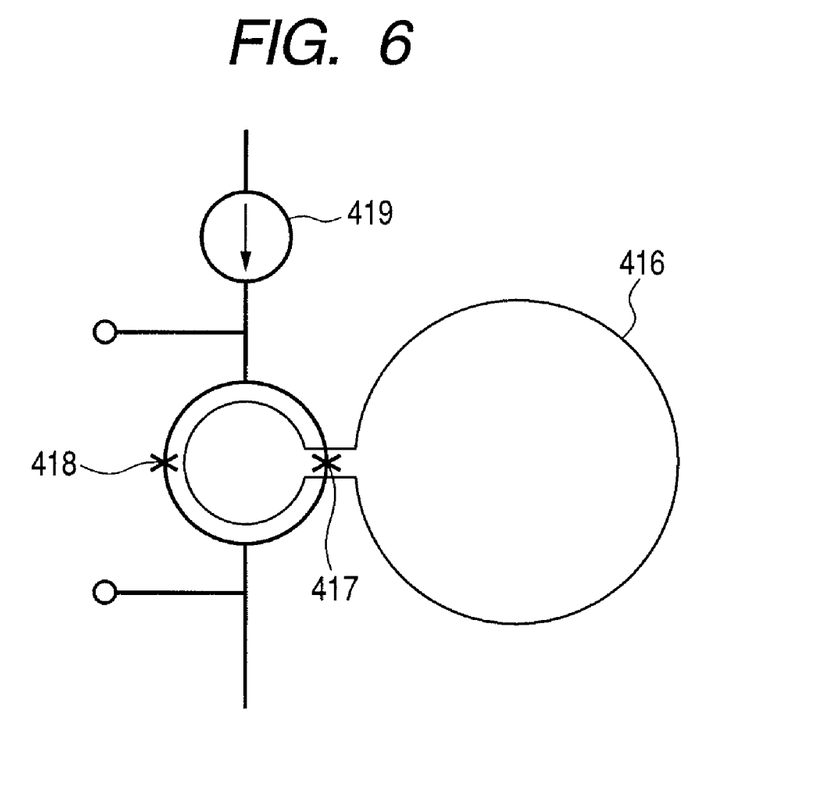
FIG. 6 is a conceptual diagram for describing a configuration of a magnetic sensor which combines a superconducting quantum interference device and detection coil.

Superconducting quantum interference devices detect magnetic fields with high sensitivity. As shown in FIG. 5, superconducting quantum interference devices include a Josephson device which has a structure in which a tunnel barrier film 413 is sandwiched between two superconductors 414 and 415. The superconductors 414 and 415 used for the Josephson device are made, for example, of an Nb, NbN, or NbTi alloy, $Nb_3Sn$ compound, or $Nb_3Al$ compound while the tunnel barrier film is made of $Al_2O_3$ or MgO. Two Josephson devices connected in the form of a ring are connected to a constant current source. Then a voltage across the Josephson devices is measured, thereby measuring the strength of a magnetic field passing through the devices. Furthermore, as shown in FIG. 6, if two Josephson devices 417 and 418 connected in the form of a ring are connected to a constant current source 419 and a detection coil 416 is added, the accuracy of magnetic field detection can be improved. In this case, what is measured is the strength of a magnetic field passing through the detection coil.

Figure 7:
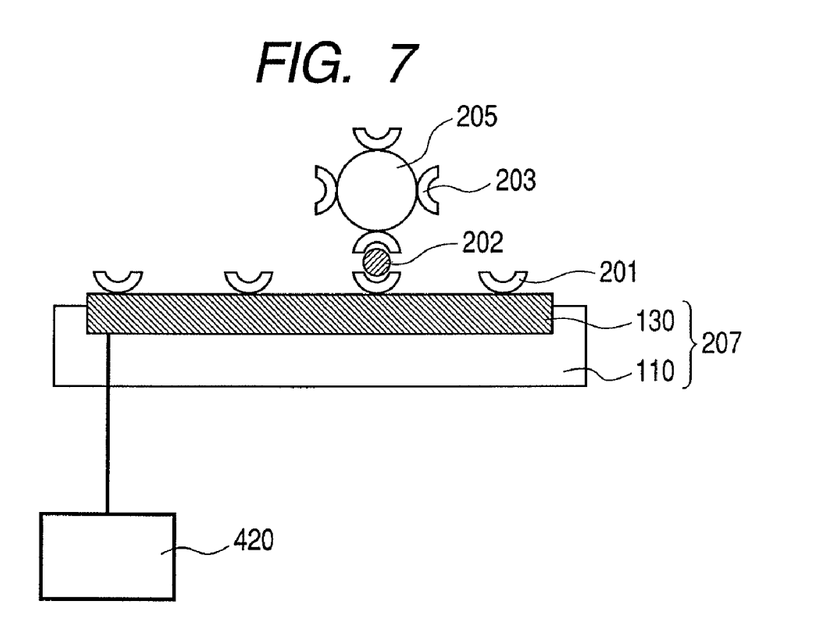
FIG. 7 is a conceptual diagram illustrating a target substance detection board.
Figure 8:
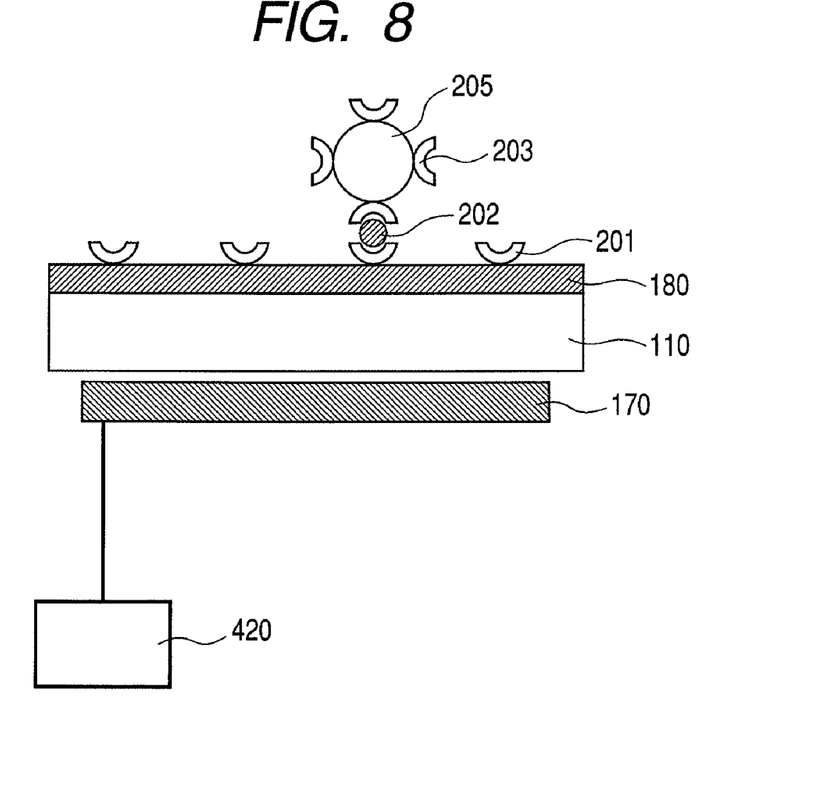
FIG. 8 is a conceptual diagram illustrating a target substance detection board.

Incidentally, the target substance detection board 207 may be constructed by mounting the magnetic sensor 130 on a surface of a support board 110 as shown in FIG. 7. Alternatively, the magnetic sensor 130 may not be mounted on a surface of the target substance detection board 207. For example, as shown in FIG. 8, the target substance detection board 207 may include a superconducting quantum interference device 170 that is a magnetic sensor, metal layer 180, and support board 110. The superconducting quantum interference device 170 may be made to detect magnetic markers fixed on a surface of the metal layer 180 (by sensing the magnetic markers at a distance from an area to which the magnetic markers are fixed). The magnetic sensor is electrically connected with a detection circuit 419 to pick up a detection signal as shown in FIGS. 7 and 8.

The first target substance capturing body 201 in FIG. 1 has a function to trap the target substance 202. The first target substance capturing body 201 and target substance 202 may be a combination of any substances such as lipid-protein, nucleic acid-protein, sugar chain-protein, cell-protein, low molecular weight compound-protein, allergen-protein, bacterium-protein, virus-protein, or nucleic acid-nucleic acid as long as the combination provides specific binding. It is assumed that a case in which a combination of A and B is represented by C-D includes both a case in which A is C and B is D and a case in which A is D and B is C.

<Magnetic Marker>

As shown in FIG. 1, the magnetic marker 206 includes the magnetic structure 205 and second target substance capturing body 203. As in the case of the first target substance capturing body 201, the second target substance capturing body 203 has a function to trap the target substance 202.

The magnetic markers 206 are fixed on the surface of the target substance detection board 207 via binding between the first target substance capturing body 201 and target substance 202 as well as between the second target substance capturing body 203 and target substance 202.

The magnetic structure 205 has its magnetization increased by polarized light 311 and generates a larger magnetic stray field than in the absence of polarized light. Any material may be used for the magnetic structure 205 as long as the material has its magnetization increased by illumination with polarized light. Available materials include (Zn, Cr) Te alloys, GaAs—Fe, and $Cr_2O_3$. In particular, GaAs—Fe and $Cr_2O_3$, which increase magnetization even at room temperature, can be used suitably. As the magnetic structure 205, any of the magnetic substances described above may be used alone or small pieces of the magnetic substances may be used in aggregate form. Size of the magnetic structure 205 is determined as appropriate depending on size of the target substance 202, reaction efficiency of the target substance 202 and second target substance capturing body 203, and the like. For example, if the target substance 202 is large in size, since a large distance between the magnetic sensor and the magnetic structure 205, the magnetic structure 205 needs to have a large particle size to increase the magnitude of the magnetic field applied to the magnetic sensor. On the other hand, if the reaction efficiency of the target substance 202 and second target substance capturing body 203 is low, it is desirable to use a magnetic structure 205 of small particle size in order to increase the reaction efficiency. Thus, the size of the magnetic structure 205 is generally in the range of 100 nm to 100 µm although the size depends on many factors.

The second target substance capturing body 203 has a function to trap the target substance 202. Desirably, the second target substance capturing body 203 and first target substance capturing body 201 trap different regions of the target substance 202. Incidentally, the second target substance capturing body 203 and first target substance capturing body 201 may be of the same type or of different types as long as the first and second target substance capturing bodies have a function to trap the target substance 202.

<Light Source>

The light source 160, which generates light to illuminate the magnetic markers 206 with polarized light, is placed in such a position as to illuminate the magnetic structure 205 of the magnetic markers with polarized light. To change the magnetization of the magnetic structure, circular polarized light is used suitably. The light source may be any device capable of emitting polarized light. Possible light sources include a polarized light emitting device which, being made up of a magnetic semiconductor or induction EL material, uses spin polarized electron injection. Alternatively, a laser source may be used in conjunction with a polarizing filter.

Next, a target substance detection method according to the present invention will be described.

The target substance detection method for detecting the presence or absence of a target substance or an amount of the target substance in a specimen, comprises: (i) putting a magnetic marker and the target substance in contact with a target substance detection board which contains a magnetic sensor and a first target substance capturing body and thereby forming a compound which includes the first target substance capturing body, the target substance, and the magnetic marker, the magnetic marker containing a magnetic structure and a second target substance capturing body; (ii) illuminating the compound with polarized light; and (iii) detecting a capturing body field generated by the magnetic structure under the polarized light.

Individual steps will be described below.

About Step (i)

Step (i) involves putting a magnetic marker and the target substance in contact with a target substance detection board which contains a magnetic sensor and a first target substance capturing body and thereby forming a compound which includes the first target substance capturing body, the target substance, and the magnetic marker, the magnetic marker containing a magnetic structure and a second target substance capturing body.

To form the compound, the target substance may be trapped in any of the following two orders: first by the second target substance capturing body of the magnetic marker and then by the first target substance capturing body, or first by the first target substance capturing body and then by the second target substance capturing body of the magnetic marker.

When the former order is used, the magnetic marker and specimen are mixed in advance and the resulting liquid mixture is placed in contact with the target substance detection board. When the latter order is used, the specimen is placed in contact with the target substance detection board and then the magnetic marker is placed in contact with the target substance detection board. Incidentally, if the magnetic marker and specimen are placed in contact with the target substance detection board simultaneously, the former and latter orders will take place simultaneously.

About Step (ii)

Step (ii) involves illuminating the compound formed in step (i) with polarized light.

The polarized light may be generated by the light source or produced by a polarizing filter using light generated by the light source. Specifically, magnetic particles to be detected are fixed on the magnetic sensor and illuminated with the polarized light, for example, intermittently.

About Step (iii)

Step (iii) involves detecting by the target substance detection board, an amount of change in a magnetic stray field generated by the magnetic structure when the magnetic stray field is illuminated with the polarized light in step (ii). The magnetic stray field is a magnetic field leaking out of a magnetic body. Strength of the magnetic stray field is proportional to the magnitude of magnetization of the magnetic structure.

The magnitude of magnetization of the magnetic structure fixed on the surface of the magnetic sensor changes under illumination with polarized light. Thus, the strength of the magnetic stray field generated by the magnetic structure also depends on the illumination with polarized light. The magnetic stray field is applied to the magnetic sensor, producing a detection signal dependent on the magnitude of magnetization of the magnetic stray field. Also, the magnetic stray field applied to the magnetic sensor increases in magnitude with increases in the number of magnetic structures, and so does the detection signal. Thus, the number of magnetic structures can be learned from the magnitude of the detection signal. This means that if relationship between quantities of the magnetic structures and target substance is known in advance, the quantity of the target substance can be learned indirectly. On the other hand, if there is no target substance, since the magnetic structure which changes the magnitude of its magnetization with illumination of the polarized light is not fixed on the surface of the magnetic sensor, the detection signal remains constant regardless of whether the magnetic structure is illuminated with the polarized light.

Also, the magnetic structure can be detected with higher accuracy if illumination with polarized light is repeated in a desired cycle. For example, a cycle of illumination and non-illumination is repeated: illumination with polarized light of a fixed intensity is provided for time T and then light illumination is not provided for the same length of time T. Consequently, magnetization of the magnetic structure increases in synchronization with the timing, and so does the strength of the magnetic stray field. Thus, by watching a frequency component of the polarized-light illumination in the magnetic-field detection signal, the magnetic field can be detected with high sensitivity at reduced noise intensity. Incidentally, if the detection signal output from the magnetic sensor is affected by the polarized light, it is advisable, for example, to form a light-shielding film between the magnetic sensor and light source to prevent the magnetic sensor from being illuminated with the polarized light.

EXAMPLES

Example 1

An example of detecting prostate-specific antigen (PSA) as a target substance will be described in the present Example. A TMR device 130 is used as the magnetic sensor and a ferromagnetic body made of GaAs—Fe is used as the magnetic structure.

The TMR device is similar in structure to a GMR device, but the GMR device uses a metal film as a non-magnetic film formed between two magnetic bodies whereas the TMR device uses a tunnel dielectric film. According to the present invention, in addition to the TMR device, various types of magnetic sensors are available for use, including GMR devices, other magnetoresistive devices, and Hall devices.

Also, materials of the magnetic structure are not limited to those described herein. Any material may be used as long as the material changes the magnitude and direction of its magnetization when illuminated with polarized light.

Figure 9:
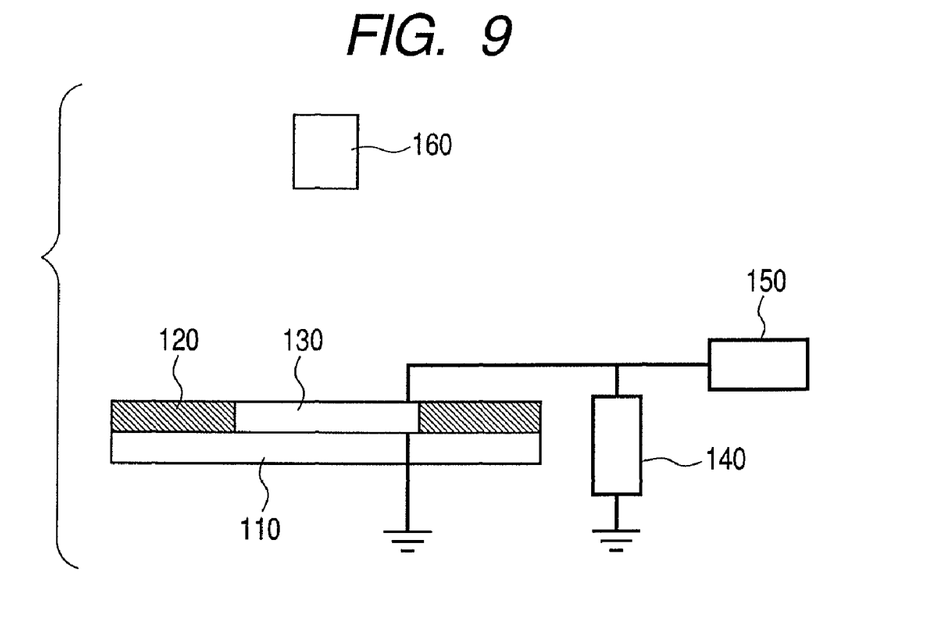
FIG. 9 is a conceptual diagram illustrating a target substance detection board used in Example 1.

FIG. 9 is a conceptual diagram for describing a target substance detection board used in Example 1. Referring to FIG. 9, a TMR device 130 is formed on a support board 110, and area other than top of the TMR device 130 is covered with a $SiO_2$ film 120. The TMR device 130 is connected with a power source 140 and detection circuit 150, where the power source 140 passes an electric current in a direction perpendicular to a film surface and the detection circuit 150 detects a potential difference between upper side (free layer) and lower side (pinned layer) of a tunnel film. Also, a light source 160 of polarized light is installed above the TMR device 130—which is a magnetic sensor—and emits the polarized light in the direction perpendicular to the film surface of the magnetic sensor.

Figure 10:
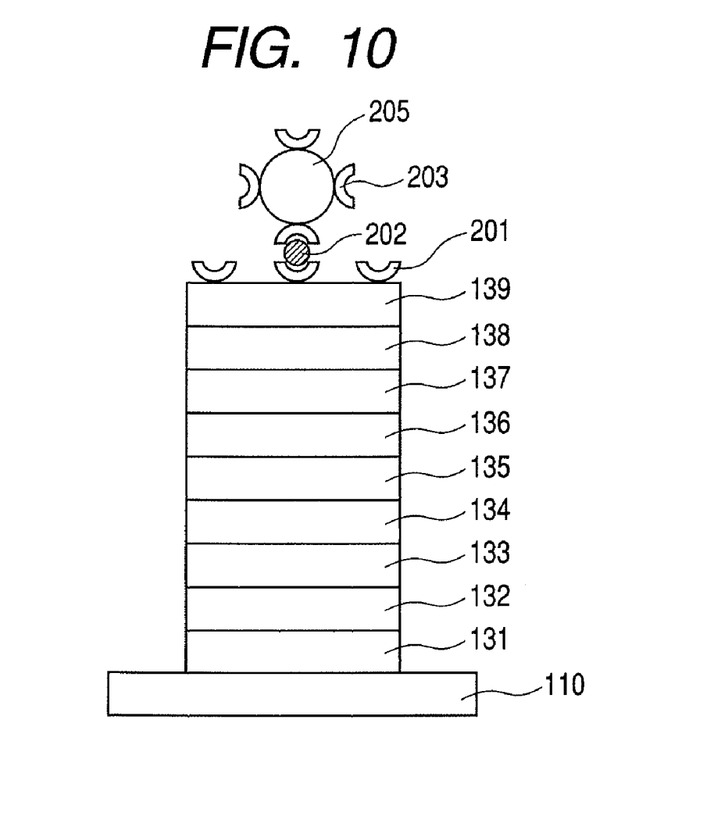
FIG. 10 is a conceptual diagram illustrating a film configuration of a TMR device 130 used as a magnetic sensor according to Example 1 and an arrangement of the TMR device 130 in relation to a magnetic structure.

FIG. 10 is a conceptual diagram illustrating a film configuration of the TMR device 130 used as a magnetic sensor according to Example 1 and an arrangement of the TMR device 130 in relation to a magnetic particle. An artificial antiferromagnetic film is created under an MgO film 136—which is a tunnel dielectric film—and used as a pinned layer. In the pinned layer, an MnIr film 132, FeCo film 133, Ru film 134, and FeCoB film 135 are stacked in sequence on a lower electrode. The two magnetic films 133 and 135 are magnetically coupled and their magnetization directions are always antiparallel to each other. Consequently, magnetostatic coupling between the pinned layer and free layer is weak.

An FeCoB film 137 is placed on the MgO film 136 to serve as the free layer. Any conductive material may be used for the lower electrode 131 as long as the conductive material does not degrade characteristics of the magnetoresistive device, and an Hf film is used according to the present Example. A Pt film 138 is formed as a protective film in the upper part of the magnetoresistive device to prevent corrosion in downstream processes. Any conductive material may be used for the upper electrode as long as the conductive material does not degrade characteristics of the magnetoresistive device, and an Au film 139 is used according to the present Example. According to the present Example, the upper electrode combines a fixing layer. To support a primary antibody 201 on the TMR device 130, a surface of the Au film 139 is treated to improve affinity for water and then treated with an aminosilane coupling agent.

The area other than the top of the TMR device 130 is covered with the $SiO_2$ film 120 so that the antibody will not be fixed on any area other than the top of the device.

According to Example 1, the target substance is detected using the target substance detection board shown in FIG. 1.

The primary antibody 201 to trap a desired antigen is fixed to the surface of the Au film 139 treated with the aminosilane coupling agent. The primary antibody 201 is fixed using a crosslinking agent such as glutaraldehyde through chemical bonding between an amino group derived from the aminosilane coupling agent and a peptide chain.

A prostate-specific antigen (PSA) 202 known as a marker for prostate cancer can be detected according to the following protocol using the target substance detection board which includes the TMR device 130 mounted on a support board 110. The primary antibody 201 used to recognize the PSA 202 has been fixed to the target substance detection board.

(1) The target substance detection board is immersed in phosphate-buffered physiological saline (test solution) containing PSA 202 which is an antigen (object under study) and incubated for five minutes.

(2) Next, any unreacted PSA 202 is washed with phosphate-buffered physiological saline.

(3) The target substance detection board which has gone through processes (1) and (2) is immersed in phosphate-buffered physiological saline containing anti-PSA antibody (secondary antibody) 203 marked by magnetic particles 205 and is incubated for five minutes.

(4) Next, any unreacted marked antibody is washed with phosphate-buffered physiological saline.

According to the above protocol, the magnetic particles 205 are fixed to the device surface via the anti-PSA antibody (secondary antibody) 203, antigen 202, and primary antibody 201. Since the magnetic particles 205 are not fixed to the top of the TMR device 130 if there is no antigen 202 in the object under study, the antigen 202 can be detected based on the presence or absence of magnetic particles 205. Also, the magnitude of the detection signal from the TMR device 130 allows the number of fixed magnetic particles 205 to be identified and indirectly indicates the quantity of the antigen 202 contained in the object under study.

For detection, the top of the TMR device 130 is illuminated with polarized light 311 from the light source 160.

Figure 11:
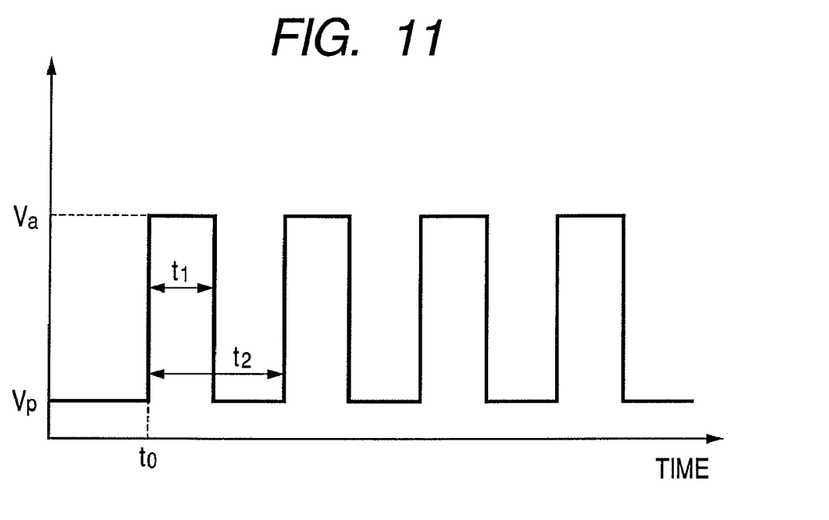
FIG. 11 is a timing chart for describing a detection signal from a sensor according to Example 1.

FIG. 11 is a timing chart for describing a detection signal from the target substance detection board according to Example 1. In an initial state, the detection signal is at a voltage Vp. The voltage of the detection signal corresponds to a potential difference across the TMR device 130.

From time t0 to t1, clockwise circular polarized light 311 is emitted. Consequently, the magnetization 204 of the magnetic particles 205 tilts downward as shown in FIG. 1. This causes the detection signal of the TMR device 130 to rise to a voltage Va. Next, the emission of the polarized light 311 is stopped, causing the magnetization 204 to return to its initial state. Consequently, the detection signal of the TMR device 130 returns to the initial voltage Vp as well.

When the circular polarized light is emitted and stopped in a cycle of t2, the direction of the magnetic stray field generated by the magnetic particles 205 changes in sync and consequently a detection signal is obtained from the TMR device 130 as shown in FIG. 11.

Example 2

According to Example 1 described above, magnetic particles are fixed on a magnetic sensor via a target substance, but it is not strictly necessary to fix the magnetic particles on the magnetic sensor. In Example 2, an example in which a superconducting quantum interference device is used as a magnetic sensor will be described.

Figure 12:
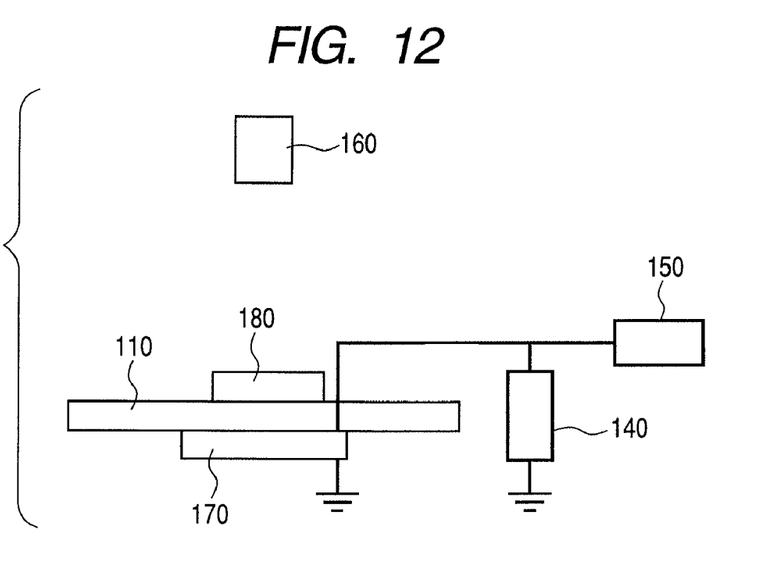
FIG. 12 is a conceptual diagram for describing a configuration of a sensor according to Example 2.

FIG. 12 is a conceptual diagram for describing a configuration of the sensor according to Example 2. According to Example 2, the superconducting quantum interference device 170 is installed under a support board 110 subjected to surface oxidation treatment. Also, an Au film 180 is formed on top of the support board 110 so that a primary antibody (first target substance capturing body) can be fixed to the support board 110. The rest of the configuration is the same as Example 1 shown in FIG. 1.

Also, the protocol used to support the primary antibody on the support board 110 is the same as Example 1. A surface of the Au film 180 is treated to improve affinity for water and then treated with an aminosilane coupling agent. Furthermore, the primary antibody is fixed using a crosslinking agent such as glutaraldehyde through chemical bonding between an amino group derived from the aminosilane coupling agent and a peptide chain. This provides a target substance detection board with the primary antibody fixed to trap a desired antigen.

The prostate-specific antigen (PSA) known as a marker for prostate cancer can be detected according to the following protocol using the target substance detection board. The primary antibody used is such that will allow the PSA to be recognized.

(1) The detection sensor is immersed in phosphate-buffered physiological saline (test solution) containing PSA which is an antigen (object under study) and incubated for five minutes.

(2) Next, any unreacted PSA is washed with phosphate-buffered physiological saline.

(3) The detection sensor which has gone through processes (1) and (2) is immersed in phosphate-buffered physiological saline containing anti-PSA antibody (secondary antibody) marked by magnetic particles and is incubated for five minutes.

(4) Next, any unreacted marked antibody is washed with phosphate-buffered physiological saline.

According to the above protocol, the magnetic particles are fixed to the surface of the Au film 180 via the anti-PSA antibody (secondary antibody and second target substance capturing body), antigen, and primary antibody. Since the magnetic particles are not fixed to the top of the Au film 180 if there is no antigen in the object under study, the antigen can be detected based on the presence or absence of magnetic particles. Also, the magnitude of a detection signal from the superconducting quantum interference device 170 allows the number of fixed magnetic particles to be identified and indirectly indicates the quantity of the antigen contained in the object under study.

According to the present Example, for detection, the light source 160 emits a clockwise circular polarized light first, and then a counterclockwise circular polarized light.

Figure 13:
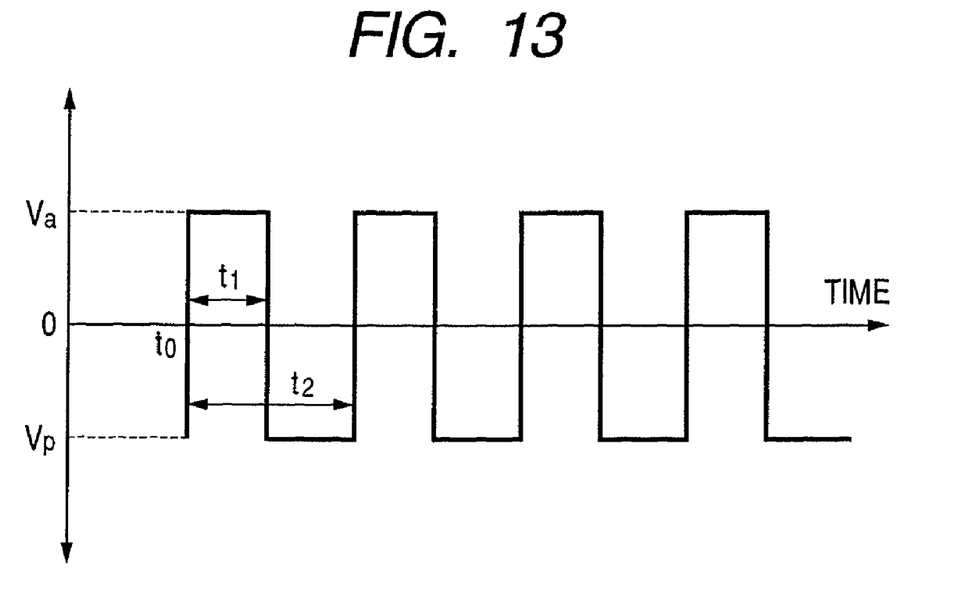
FIG. 13 is a timing chart for describing a detection signal from the sensor according to Example 2.

FIG. 13 is a timing chart for describing the detection signal from the sensor according to Example 2. Voltage of the detection signal corresponds to a potential difference across the superconducting quantum interference device 170.

Referring to FIG. 13, the clockwise circular polarized light is emitted from time t0 to t1, causing the magnetization 204 of the magnetic particles 205 to tilt downward in FIG. 1. Consequently, the voltage of the detection signal from the superconducting quantum interference device 170 rises to Va. Next, the counterclockwise circular polarized light is emitted, causing the magnetization 204 to tilt in the opposite direction, i.e., upward in FIG. 1. Consequently, the voltage of the detection signal from the superconducting quantum interference device 170 falls to Vp.

When the emission of the clockwise circular polarized light and counterclockwise circular polarized light is repeated in a cycle of t2, the direction of the magnetic stray field generated by the magnetic particles changes in sync and consequently a detection signal is obtained from the superconducting quantum interference device 170 as shown in FIG. 13.

The sensor described above can detect magnetic bodies without applying a magnetic field to the magnetic particles and can detect magnetic fields with high accuracy. Conventionally, the use of the superconducting quantum interference device involves orienting the device precisely with respect to the magnetic fields to make the device insensitive to the external magnetic field. On the other hand, the present Example, which does not involve the application of a magnetic field, does not require high accuracy in the orientation of the superconducting quantum interference device. Furthermore, if magnetic bodies are modified, the superconducting quantum interference device according to the present Example can be used to detect biological material and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-145288, filed May 31, 2007, which is hereby incorporated by reference herein in its entirety.

What is claimed is:

1. A target substance detection method for detecting the presence or absence of a target substance or an amount of the target substance in a specimen, comprising:
   (i) putting a magnetic marker and the specimen in contact with a target substance detection board which contains a magnetic sensor and a first target substance capturing body and thereby forming a compound which includes the first target substance capturing body, the target substance, and the magnetic marker, the magnetic marker containing a magnetic structure and a second target substance capturing body;
   (ii) illuminating the compound with polarized light; and
   (iii) detecting a magnetic stray field generated by the magnetic structure under the polarized light by using the magnetic sensor, so as to detect the target substance.

2. The target substance detection method according to claim 1, wherein the detecting a magnetic stray field generated by the magnetic structure under the polarized light detects changes in electrical characteristics of the magnetic sensor, the changes being caused by the magnetic stray field generated by the structure under the polarized light.

3. The target substance detection method according to claim 1, wherein the polarized light is a circular polarized light.

4. The target substance detection method according to claim 1, wherein the magnetic sensor is selected from the group consisting of a magnetoresistive device, a Hall device, and a superconducting quantum interference device.

* * * * *